United States Patent [19]

Hesse

[11] Patent Number: Plant 6,562

[45] Date of Patent: Jan. 24, 1989

[54] CHRYSANTHEMUM PLANT NAMED AMETHYST

[75] Inventor: Peter S. Hesse, Bradenton, Fla.

[73] Assignee: Ball Pan Am Plant Co., Parrish, Fla.

[21] Appl. No.: 56,984

[22] Filed: Jun. 3, 1987

[51] Int. Cl.[4] ..... A01H 5/00

[52] U.S. Cl. ..... Plt./76

[58] Field of Search ..... Plt./76

*Primary Examiner*—Robert E. Bagwill

*Attorney, Agent, or Firm*—Foley & Lardner, Schwartz, Jeffery, Schwaab, Mack, Blumenthal & Evans

[57] ABSTRACT

A Chrysanthemum plant named Amethyst, characterized by its fully double, dark lavender flowers; very long and sturdy peduncles; 9 week response.

1 Drawing Sheet

The present invention comprises a new and distinct cultivar of *Chrysanthemum morifolium,* Ramat., hereinafter referred to by the cultivar name Amethyst.

Amethyst is a product of a planned breeding program which had the objective of creating new Chrysanthemum cultivars having 9 week flower response, dark lavender decorative flowers, and suitability for a year round cut flower program. Such traits in combination were not present or needed improvement in previously available commercial cultivars.

Amethyst was originated from a hybridization made by Peter S. Hesse in a controlled breeding program in West Chicago, Ill. in 1980. The female parent was a cultivar designated SP7-611-P. The male parent of Amethyst was Beloved. Amethyst was discovered and selected as one flowering plant within the progeny of the stated parentage by applicant in November 1981 in a controlled environment in Parrish, Fla.

The first act of asexual reproduction of Amethyst was accomplished when vegetative cuttings were taken from the initial selection in April 1982 in a controlled environment in Parrish, Fla. by a technician working under formulations established and supervised by Peter S. Hesse. Horticultural examination of selected units initiated in July 1982 has demonstrated that the combination of characteristics as herein disclosed for Amethyst are firmly fixed and are retained through successive generations of asexual reproduction.

The following traits have been repeatedly observed and are determined to be basic characteristics of Amethyst, which in combination distinguish this Chrysanthemum as a new and distinct cultivar:

1. Best suited for production as a cut flower with center bud removal.
2. Dark lavender flowers.
3. Very long and sturdy peduncles, 25 cm or more.
4. Ray florets 18–38 mm in length and 8–10 mm in width.
5. Average number of ray florets per capitulum is 338.
6. Flower is fully double, very few disc florets present.
7. Diameter across face of capitulum is 6.5–8.5 cm.
8. Nine (9) week flower response.

Amethyst has not been observed under all possible environmental conditions. The phenotype may vary significantly with variations in environment such as temperature, light intensity, and day length. The following observations, measurements and comparisons describe plants grown in Parrish, Fla. under greenhouse conditions which approximate those generally used in commercial practice.

Of the many commercial cultivars known to the present inventor, the most similar in comparison to Amethyst is Organdy, disclosed in U.S. Plant Pat. No. 5,278. Reference is made to attached Chart A which compares certain characteristics of Amethyst to those same characteristics of Organdy. In comparison to Organdy, Amethyst has larger and more dense lavender colored flowers. The flower color of Organdy is pink.

The accompanying photographic drawing shows typical inflorescence and foliage characteristics of Amethyst. The photograph is in black and white, with one flower being colored to accurately depict true flower color.

In the following description, color references are made to The Royal Horticultural Society Colour Chart. The color values were determined between 10:00 and 10:20 a.m. on May 15, 1987 under fluorescent light at Parrish, Fla.

Classification:

*Botanical.*—Chrysanthemum morifolium, Ramat., cv. Amethyst.

*Commercial.*—*Cut decorative spray.*

INFLORESCENCE

A. Capitulum:
- *Form.*—Flat.
- *Type.*—Double.
- *Diameter across face.*—6.5–8.5 cm.

B. Corolla of ray florets:
- *Color (general tonality from a distance of three meters).*—Dark lavender.
- *Color (upper surface).*—78B.
- *Color (under surface).*—78D.

C. Corolla of disc florets:
- *Color (mature).*—Yellow, very few present.
- *Color (immature).*—Yellow-green, very few present.

D. Reproductive organs:
- *Androecium.*—Present in disc florets only.
- *Gynoecium.*—Present in both disc and ray florets.

PLANT

A. General appearance:
- *Height.*—1½–2 meters; flowering height can differ under different growing conditions, cultural practices and applications of growth regulators.

B. Foliage:

*Color (upper surface).*—147A.

*Color (under surface).*—147B.

*Shape.*—Ovate, margins deeply lobed and serrated.

CHART A

| | AMETHYST | ORGANDY |
|---|---|---|
| Diameter across face of Capitulum | 6.5–8.5 cm | 5–6.5 cm |
| Average number ray florets per capitulum | 338 | 305 |
| Range of ray floret length | 18–38 mm | 13–29 mm |

CHART A-continued

| | AMETHYST | ORGANDY |
|---|---|---|
| Range of ray floret width | 8–10 mm | 7–9 mm |
| Flower response in weeks | 9 | 9 |
| Color of upper surface of ray florets | 78B | 68A–68D |

I claim:

1. A new and distinct cultivar of Chrysanthemum plant named Amethyst, as illustrated and described, and particularly characterized by its fully double, dark lavender flowers; very long and sturdy peduncles; and its 9 week response.

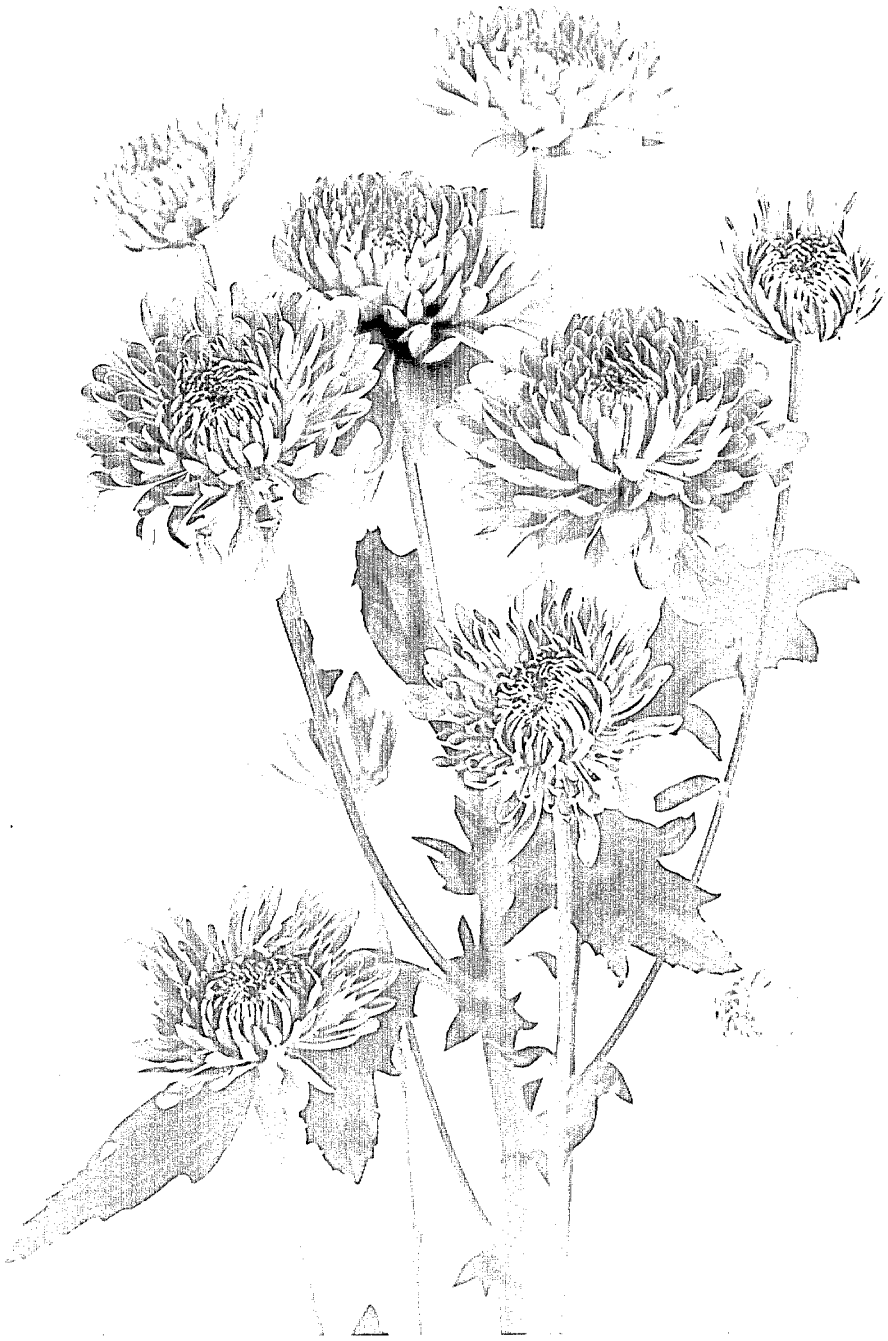

* * * * *